(12) United States Patent
van Oort et al.

(10) Patent No.: US 6,707,455 B2
(45) Date of Patent: Mar. 16, 2004

(54) METHOD FOR GRAPHICAL VISUALIZATION OF MEASURED MAGNETIC FIELD ON MRI VOLUME

(75) Inventors: Johannes Martinus van Oort, Niskayuna, NY (US); Bruce Campbell Amm, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 352 days.

(21) Appl. No.: 09/795,167

(22) Filed: Feb. 28, 2001

(65) Prior Publication Data

US 2001/0023309 A1 Sep. 20, 2001

Related U.S. Application Data

(60) Provisional application No. 60/185,794, filed on Feb. 29, 2000.

(51) Int. Cl.[7] .............................................. G06T 11/20
(52) U.S. Cl. .................................... 345/440; 345/424
(58) Field of Search ................................ 345/440, 424; 600/413; 324/329; 382/128

(56) References Cited

U.S. PATENT DOCUMENTS

| | | | |
|---|---|---|---|
| 4,899,109 A | * | 2/1990 | Tropp et al. ................ 324/320 |
| 5,045,794 A | | 9/1991 | Dorri et al. |
| 5,734,384 A | * | 3/1998 | Yanof et al. ................. 345/424 |
| 5,926,568 A | * | 7/1999 | Chaney et al. .............. 382/128 |
| 6,249,594 B1 | * | 6/2001 | Hibbard ....................... 382/128 |
| 6,266,453 B1 | * | 7/2001 | Hibbard et al. ............. 382/294 |

* cited by examiner

*Primary Examiner*—Matthew Luu
(74) *Attorney, Agent, or Firm*—Jean K. Testa; Patrick K. Patnode

(57) ABSTRACT

A method for graphical visualization of a measured magnetic field on an imaging volume of a MRI magnet includes providing data values measured at selected points of the measured magnetic field, converting each of the data values to a visualizable value based on where the data value lies within a predetermined range of data values and thus within a range of visualizable values corresponding to the range of data values, and plotting each visualizable value corresponding to each data value at a position on a grid corresponding to the position of the selected point of the measured magnetic field such that the visualizable values once plotted on the grid provide a graphical visualization of the condition of the measured magnetic field.

17 Claims, 3 Drawing Sheets

METHOD FOR GRAPHICAL VISUALIZATION OF MEASURED MAGNETIC FIELD ON MRI VOLUME

CROSS REFERENCE TO RELATED APPLICATIONS

This application claims the benefit of U.S. provisional application Ser. No. 60/185,794 filed on Feb. 29, 2000.

BACKGROUND OF THE INVENTION

The present invention generally relates to shimming a magnetic resonance imaging (MRI) magnet and more particularly is concerned with a method for graphical visualization of a measured magnetic field on an imaging volume of a MRI magnet.

A MRI magnet generates a magnetic field with a generally spherical region of high homogeneity typically referred to as the imaging volume or DSV of the magnet. The magnetic field is typically measured on this spherical region by sampling the magnetic field at points, typically equidistantly spaced apart, along its latitude and longitude. Optionally, some additional points along its axis may also be sampled.

Traditionally, the magnetic field on a DSV is represented as a list of field points in ASCII, or as a table of the spherical harmonic content of the field on the surface of the sphere (and thus also in the interior for a volume free of magnetic material). This representation, although useful for computer optimization and interpretation by codes, is not very useful in visually showing inhomogeneous regions on the DSV, or shim errors caused by misplaced shims.

Consequently, a need exists for an innovation which will provide a means to visually assess to the condition of the magnetic field and its inhomogeneities.

BRIEF SUMMARY OF THE INVENTION

The present invention provides a method for graphical visualization of a measured magnetic field on an imaging volume of a MRI magnet which is designed to satisfy the aforementioned need. The method of the present invention allows the graphical representation of the measured magnetic field in either a two-dimensional or three-dimensional format and the direct visualization of field inhomogeneities through surface texture and/or coloring schemes. In such manner, the method greatly enhances understanding of the origin of field disturbances.

In one embodiment of the present invention, a method for graphical visualization of a measured magnetic field on an imaging volume of a MRI magnet is provided which comprises the steps of providing data values measured at selected points of a measured magnetic field on an imaging volume of a MRI magnet, converting each of the data values to a visualizable value based on where the data value lies within a preset range of data values and thus within a range of visualizable values corresponding to the range of data values, and plotting each visualizable value corresponding to each data value at a position on a grid corresponding to the position of the selected point of the measured magnetic field on the imaging volume such that the visualizable values once plotted on the grid provide a graphical visualization of the condition of the measured magnetic field on the imaging volume of the MRI magnet.

The grid can be either of planar configuration or spherical configuration. In the spherical configuration of the grid, the method further comprises the step of rotating the spherical grid to highlight selected areas of the magnetic field.

DETAILED DESCRIPTION OF THE INVENTION

Figure 1:
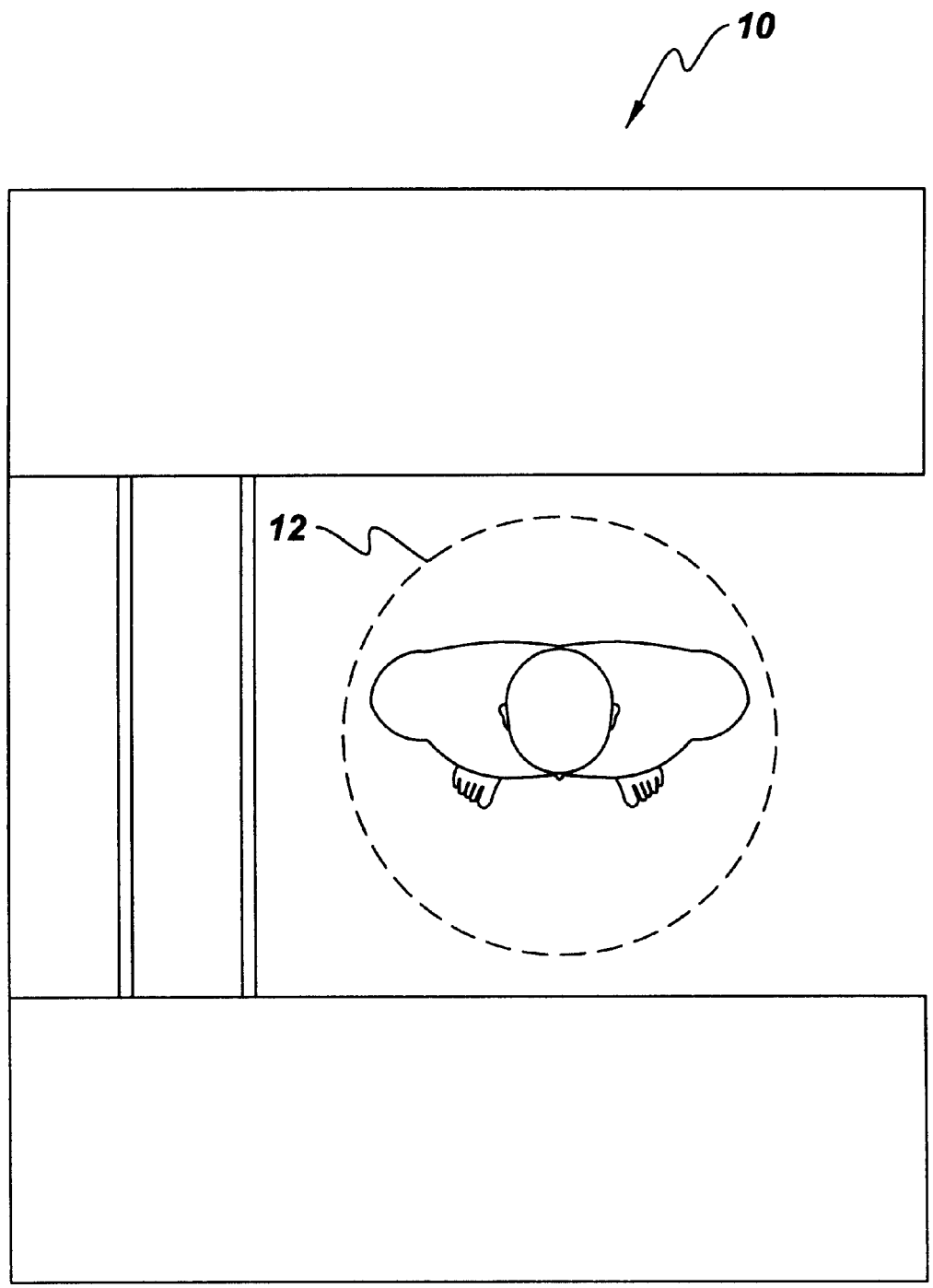
FIG. 1 is a schematic view of an open MRI magnet having a measured magnetic field on an imaging volume which can be graphically visualized by the method of the present invention.

Referring now to the drawings and particularly to FIG. 1, there is illustrated a schematic representation of an open MRI magnet, generally designated 10, which generates a magnetic field having a region of high homogeneity which is typically referred to as a magnetic resonance imaging volume 12 (seen as a dotted line in FIG. 1). The imaging volume 12 is generally spherical in configuration. The magnetic field is typically measured on the imaging volume 12 by sampling the magnetic field at points, typically equidistantly spaced apart, along its latitude and longitude. Optionally, some additional points along its axis may also be sampled.

Figure 2:
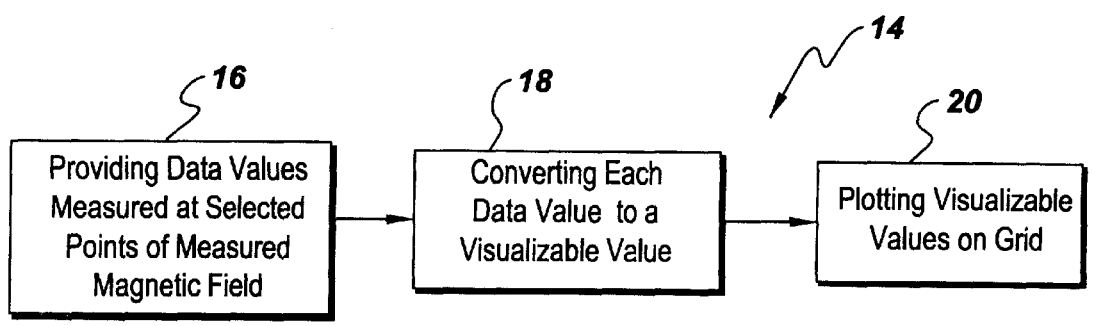
FIG. 2 is a flow diagram of the steps of the method for graphical visualization of the measured magnetic field on the imaging volume of the MRI magnet.

Referring to FIG. 2, there is illustrated in a flow chart, generally designated 14, the steps of the method of the present invention for graphical visualization of the measured magnetic field on the imaging volume 12 of the MRI magnet 10. Block 16 of the flow chart 14 represents the step of providing data values measured at selected points of the measured magnetic field on the imaging volume 12. Block 18 of the flow chart 14 represents the step of converting each of the data values to a visualizable value based on where the data value lies within a preset range of data values and thus within a range of visualizable values corresponding to the range of data values. Block 20 of the flow chart 14 represents the step of plotting each visualizable value corresponding to each data value at a position on a grid corresponding to the position of the selected point of the measured magnetic field on the imaging volume 12 such that the visualizable values once plotted on the grid provide a graphical visualization of the condition of the measured magnetic field on the imaging volume 12 of the MRI magnet 10. The grid 22 can be of planar configuration as depicted in FIG. 3 or the grid 24 can be of spherical configuration as depicted in FIG. 4.

Figure 3:
FIG. 3 is a two-dimensional visualization of the measured magnetic field on the imaging volume of the MRI magnet.

Referring to FIG. 3, the data values measured at the selected points of the measured magnetic field on the spherical imaging volume 12 are displayed as a mercator projection or grid 22, in either a range of colors or a grayscale ranging from light to dark, where each color or shade of gray corresponds to a small range of data between the minimum and maximum values. The data values can be displayed with the lines of longitude in either columns or rows. If any axis points are measured, they can be displayed as an additional row or column. Additionally, a color bar is added that shows what range of values each color or shade used to generate the grid corresponds to. This manner of display can also be used for any surface of revolution, not just spheres, such as ellipsoids. It can also be used to display synthetic or theoretical data and not just measured data.

Figure 4:
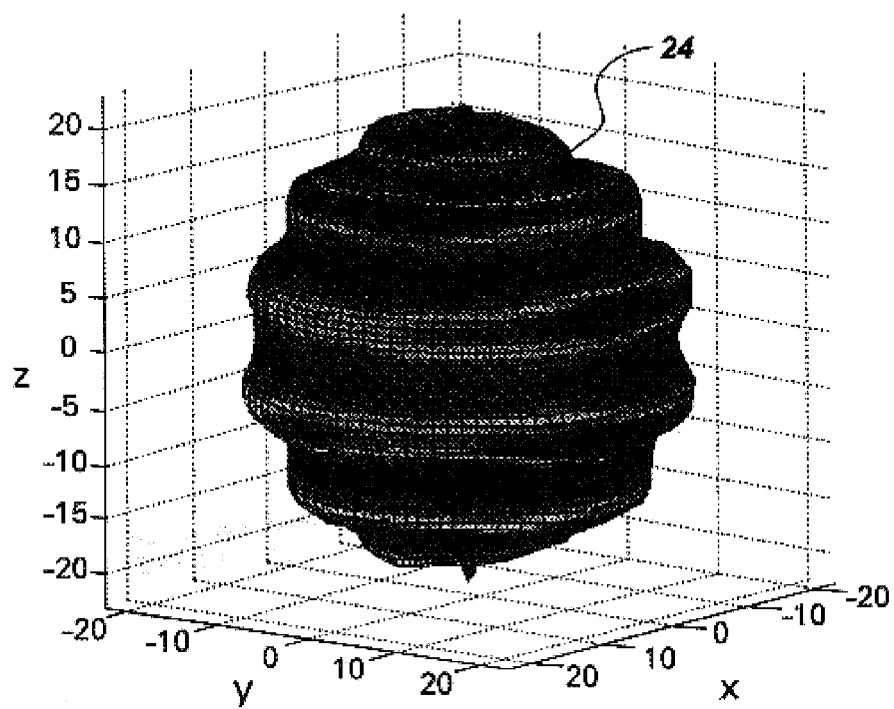
FIG. 4 is a three-dimensional visualization of the measured magnetic field on the imaging volume of the MRI magnet.

Referring to FIG. 4, the data values measured at the selected points of the measured magnetic field on the spherical imaging volume 12 are displayed as the spherical projection or grid 24, in either a range of colors or a grayscale ranging from light to dark, where each color or shade of gray corresponds to a small range of data between the minimum and maximum values, or as surface relief. For example, a color value is generated for each location on the sphere, based on the deviation of the magnetic field from the average field (or the central field in the DSV). A magnitude of the deviation can also be used to compute a surface relieve, that is, a surface expansion or contraction of the sphere. Either value, or both, are now used to create a spherical projection of the magnetic field, that can be rotated at will to look at a specific region of the DSV.

For computation of the magnetic field in the interior of the sphere, the field can be decomposed into spherical harmonic terms or values. Once the decomposition is done, a recomposition can be performed on a sphere with an arbitrary radius. The recomposed field can be used to show the influence of a shim on the interior volume, which is far more important for final IQ in nMR imaging. The decompose and recompose steps can also be used to artificially increase the number of sampling points on the sphere to create smoother plots, or better convergence in the shimming algorithm.

In summary, to rapidly assess the condition of the magnetic field and its homogeneity, the method of the present invention, using either color or grayscale graphing, provides either: (1) a two-dimensional mercator projection or plotting of the field magnitude or inhomogeneity onto the rectangular grid 22 or (2) a three-dimensional projection or plotting onto the spherical grid 24. In the case of the spherical grid 24, the graphical visualization of field inhomogeneity can be enhanced by using surface relief in addition, or as an alternative, to color and grayscale graphing. Both two-dimensional and three-dimensional graphical visualization will enable one to quickly assess the condition, i.e. shape and location, of field homogeneity or shim errors, and also to plot the influence of shims on the magnetic field of the imaging volume 12.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

What is claimed is:

1. A method for graphical visualization of a measured magnetic field on an imaging volume of a MRI magnet, comprising the steps of:

providing data values measured at selected points of a measured magnetic field on an imaging volume of a MRI magnet;

converting each of the data values to a visualizable value based on where the data value lies within a preset range of data values and thus within a range of visualizable values corresponding to the range of data values; and plotting each visualizable value corresponding to each data value at a position on a grid corresponding to the position of the selected point of the measured magnetic field on the imaging volume such that the visualizable values once plotted on the grid provide a graphical visualization of the condition of the measured magnetic field on the imaging volume of the MRI magnet.

2. The method of claim 1 in which the data values are polar data values at different radii of the imaging volume.

3. The method of claim 1 in which each of said visualizable values is a particular color within a range of different colors.

4. The method of claim 1 in which each of said visualizable values is a particular shade of gray within a grayscale range of from light to dark.

5. The method of claim 1 in which the grid is of planar configuration.

6. The method of claim 5 in which each of said visualizable values is a particular color within a range of different colors provided on the grid of planar configuration.

7. The method of claim 5 in which each of said visualizable values is a particular shade of gray within a grayscale range of from light to dark provided on the grid of planar configuration.

8. The method of claim 5 in which the grid is of rectangular configuration.

9. The method of claim 1 in which the selected points of the measured magnetic field are measured along the latitude and longitude of the imaging volume.

10. The method of claim 9 in which the selected points are equidistantly spaced apart.

11. The method of claim 1 in which the grid is of spherical configuration.

12. The method of claim 11 in which each of said visualizable values is a particular color within a range of different colors provided on the grid of spherical configuration.

13. The method of claim 11 in which each of said visualizable values is a particular shade of gray within a grayscale range of from light to dark provided on the grid of spherical configuration.

14. The method of claim 11 in which each of said visualizable values is a particular surface relief provided on the grid of spherical configuration.

15. The method of claim 11 further comprising the step of:

rotating the grid of spherical configuration to highlight selected areas of the magnetic field.

16. The method of claim 11 in which said converting includes decomposing the data values into spherical harmonic values.

17. The method of claim 16 in which said plotting includes recomposing the spherical harmonic values onto a sphere with an arbitrary radius.

* * * * *